United States Patent [19]

King et al.

[11] 3,984,293

[45] Oct. 5, 1976

[54] PROCESS OF REDUCTION

[75] Inventors: Ronald Joseph King, Wareside; George Raymond White, Harpenden, both of England

[73] Assignee: Smith Kline & French Laboratories Limited, Welwyn Garden City, England

[22] Filed: Aug. 6, 1975

[21] Appl. No.: 602,332

[30] Foreign Application Priority Data

Sept. 2, 1974 United Kingdom............... 38259/74

[52] U.S. Cl.................................... 204/75; 204/72; 204/73 R; 204/77
[51] Int. Cl.$^2$.................. C25B 3/04; C07D 233/14
[58] Field of Search................ 204/72, 73 R, 75–77

[56] References Cited

UNITED STATES PATENTS 815,193  3/1906  Mettler................................ 204/75

OTHER PUBLICATIONS

Iversen et al., Acta Chem. Scand., vol. 21, pp. 279–285, (1967).
Ferles et al., Chem. Abst., vol. 54, abst. 4575g.

*Primary Examiner*—F.C. Edmundson
*Attorney, Agent, or Firm*—Joan S. Keps; Richard D. Foggio; William H. Edgerton

[57] ABSTRACT

An electrochemical process for preparing 4-(hydroxymethyl)-imidazoles, which are useful as chemical intermediates.

6 Claims, No Drawings

PROCESS OF REDUCTION

This invention relates to an improved process of reduction for the production of imidazole derivatives. In particular it relates to an improved process for the production of 4-(hydroxymethyl)imidazole derivatives which are useful intermediates for the production of pharmacologically active compounds.

4-Imidazolecarboxylic acids and esters may be reduced to 4-(hydroxymethyl)imidazoles using lithium aluminium hydride but the process is expensive and may be inconvenient. It has been reported that substituted benzoic acids may be electrochemically reduced to benzyl alcohols, e.g. (Mettler, Ber 1905, 38 1745; 1906, 39 2937) but the analogous process has not been reported commencing with heterocyclic carboxylic acids.

Ferles and Prystas (Coll. Czech. Chem. Comm. 1959, 24 3326) reported that the electrochemical reduction of 2-pyridinecarboxylic acid gave mainly 2-methylpyridine, 2-methylpipecoline, 2-methyl-1,2,3,6-tetrahydropyridine; and Iversen and Lund (Acta Chem. Scand. 21, 279, (1967)) reported that 2-imidazolecarboxylic acid was polarographically reduced to the corresponding aldehyde, and that 4-imidazolecarboxylic acid was not polarographically reducible. Surprisingly, we have discovered that 4-imidazolecarboxylic acids can be conveniently reduced electrochemically to the corresponding 4-(hydroxymethyl)imidazole derivatives.

Throughout this specification and claims by the term lower alkyl we mean an alkyl group containing from one to four carbon atoms.

Accordingly we provide a process wherein a 4-imidazolecarboxylic acid of Formula I

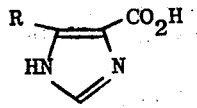

FORMULA I wherein R is hydrogen or lower alkyl, is reduced electrochemically to the corresponding 4-(hydroxymethyl)imidazole of Formula II

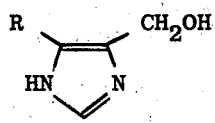

FORMULA II wherein R is hydrogen or lower alkyl such as methyl. The reduction is carried out in a suitable protic solvent using a cathode, such as a lead or mercury cathode, which has a high hydrogen overvoltage and which is inert to the electrolyte, under controlled current and voltage conditions such that hydrogen is evolved at the cathode. A suitable current density at the cathode is often in the region of 0.1 amp cm$^{-2}$, and the applied voltage depends, of course, on the resistance of the cell but is often in the region of 6–10 volts. The voltage is applied for a suitable period of time, e.g., 3 to 12 hours.

Suitable protic solvents include aqueous solutions of strong acids such as sulphuric acid, hydrochloric acid, hydrobromic acid, phosphoric acid, perchloric acid, trifluoroacetic acid and trichloroacetic acid. The strong acid used should not interfere with the electrochemical reduction. If necessary the solvent is stirred, and the process is carried out at suitable temperatures, such as 25°–75° C.

Conveniently the solution of the 4-imidazolecarboxylic acid is placed in a cathodic compartment which is separated by a glass frit from the anodic compartment which contains only solvent.

The anode may be made from any suitable material for example carbon or platinum. The 4-imidazolecarboxylic acid may be derived from an ester e.g. the ethyl ester since this is the product of a convenient method of synthesis. In this case acid hydrolysis of the ester is first carried out and the resultant solution used directly in the electrochemical process of the present invention without any further purification.

It will be understood that the compounds produced and used as starting materials in the process of our invention may exist in the form of acid addition salts.

The compounds of Formula II are useful as intermediates for the production of pharmacologically active compounds, in particular histamine H$_2$-antagonists, for example N-methyl-N'-[2-((5-R-4-imidazolyl)methylthio)ethyl]thiourea and N-cyano-N'-methyl-N''-[2-((5-R-4-imidazolyl)methylthio)ethyl]guanidine compounds. Histamine H$_2$-antagonists act at histamine H$_2$-receptors which as described by Black et al. (Nature, 1972,236,385) may be defined as those histamine receptors which are not blocked by "antihistamines" such as mepyramine but are blocked by burimamide. Blockade of histamine H$_2$-receptors is of utility in inhibiting the biological actions of histamine which are not inhibited by antihistamines. Histamine H$_2$-antagonists are useful, for example, as inhibitors of gastric acid secretion.

N-Methyl-N'-[2-((5-R-4-imidazolyl)methylthio)ethyl]thioureas are prepared from the 5-R-4-(hydroxymethyl)imidazoles of Formula II by reacting the hydroxymethyl compound with cysteamine and then reacting the resulting 5-R-4-[(2-aminoethyl)thiomethyl]imidazole with methyl isothiocyanate.

N-Cyano-N'-methyl-N''-[2-(5-R-4-imidazolyl)methylthio)ethyl]guanidines are prepared from the 5-R-4-(hydroxymethyl) imidazoles of Formula II by reacting the hydroxymethyl compound with cysteamine and then reacting the resulting 5-R-4-[(2-aminoethyl)thiomethyl]imidazole with N-cyano-N',-S-dimethylisothiourea or by reacting the 5-R-4-[(2-aminoethyl)thiomethyl]imidazole compound with dimethyl-N-cyanoimidodithiocarbonate and reacting the resulting N-cyano-N'-[2-((5-methyl-4-imidazolyl)methylthio)ethyl]-S-methylisothiourea with methylamine.

These thiourea and cyanoguanidine products prepared from the intermediates of Formula II are described in British Patent No. 1,338,169.

The invention is illustrated but in no way limited by the following examples, wherein all temperatures are given in degrees Centigrade.

EXAMPLE 1

An electrolysis vessel had two compartments separated by a glass frit; the cathodic compartment contained a pool of mercury of 13.3 cm$^2$ area which acted as cathode, and the other compartment contained an anode of platinum wire. A solution of 4-imidazolecarboxylic acid (0.56 g) in hydrochloric acid (1.0N, 30 cc) was placed in the cathodic compartment and 1.0N hydrochloric acid was placed in the anodic compartment. The material in the cathodic compartment was stirred, and the mixture was electrolysed for 4½ hours at a constant current of 1.5 amps and a potential difference of 8–10 volts between the electrodes. Much hydrogen was evolved at the cathode, and the solution warmed up to 65°. The solution in the cathodic compartment was removed, passed down an ion-exchange column (IRA-400 in the OH⁻ form) and eluted with water. The eluate was evaporated to a solid residue which was triturated with petroleum ether (b.p. 40°–60°) to give 4-(hydroxymethyl)imidazole (0.22 g) m.p. 88°–91°.

EXAMPLE 2

A solution of 4-imidazolecarboxylic acid (0.56 g) in 25% v/v sulphuric acid (25 cc) was placed in the cathodic compartment of a vessel as described in example 1, and 25% v/v sulphuric acid was placed in the anodic compartment. The mixture was electrolysed for 3½ hours under conditions similar to those described in Example 1. The solution from the cathodic compartment was neutralised with potassium carbonate (18.5 g) and the mixture was evaporated to dryness. The solid residue was extracted with hot isopropanol (200 cc) and the extract was evaporated to an oil which was crystallised from ether to give 4-(hydroxymethyl)imidazole (0.42 g) m.p. 66°–80°. The picrate derivative of this material was recrystallised from water and had m.p. 205.5°.

EXAMPLE 3

A solution of 5-methyl-4-imidazolecarboxylic acid, ethyl ester (2.0 g) in 25% v/v sulphuric acid (25 cc) was heated under reflux overnight. This solution was cooled and was placed in the cathodic compartment of a vessel as described in Example 1, and 25% v/v sulphuric acid was placed in the anodic compartment. The mixture was electrolysed for 4 hours under conditions similar to those described in Example 1. The solution from the cathodic compartment was neutralised with potassium carbonate and the mixture was evaporated to dryness. The solid residue was extracted with hot isopropanol (250 cc) and the extract was evaporated to low volume. Excess ethanolic hydrogen chloride was added and the solution was evaporated to dryness. The residue was triturated with ether to give 4-(hydroxymethyl)-5-methylimidazole hydrochloride (0.96 g) m.p. 250°–265° (decomp.), which appeared by thin-layer chromatography and infra-red spectroscopy to be identical to an authentic sample.

EXAMPLE 4

An electrolysis vessel had two compartments separated by a glass frit; the cathodic compartment contained a cathode of pure (>99.95%) lead of 9.3 cm² area, and the other compartment contained an anode of platinum wire. A solution of 5-methyl-4-imidazolecarboxylic acid hydrate (1.26 g) in 25% v/v sulphuric acid (25 cc) was placed in the cathodic compartment and was stirred, and 25% v/v sulphuric acid was placed in the anodic compartment. The mixture was electrolysed for 4½ hours at a constant current of 1.2 amp and a potential difference of 6–7 volts between the electrodes. Much hydrogen was evolved at the cathode, and the solution warmed up to 55°. The solution from the cathodic compartment was neutralised with potassium carbonate and the mixture was evaporated to dryness. The solid residue was extracted with hot isopropanol (250 cc) and the extract was evaporated to low volume. Excess ethanolic hydrogen chloride was added and the mixture was evaporated to dryness. The residue was dissolved in water, passed down an ion-exchange column IRA-400 in the OH⁻ form) and eluted with water. The eluate was evaporated to a solid residue which was triturated with petroleum ether (b.p. 40°–60°) to give 4-hydroxymethyl-5-methylimidazole (0.14 g) m.p. 114°. A sample of the hydrochloride of this material was recrystallised from ethanol-ether and had m.p. 240°–2°.

EXAMPLE 5

When 5-butyl-4-imidazolecarboxylic acid is substituted for 5-methyl-4-imidazolecarboxylic acid in the general procedure of Example 4, 4-hydroxymethyl-5-butylimidazole is produced.

EXAMPLE 6

A solution of 4-hydroxymethyl-5-methylimidazole hydrochloride (30.0 g) and cysteamine hydrochloride (23.0 g) in acetic acid (200 ml) was heated under reflux for 10 hours. Following cooling to 15°–20°, the solid which crystallised was collected and washed with isopropyl alcohol to give 4-methyl-5-[(2-aminoethyl)-thiomethyl]imidazole dihydrochloride m.p. 189°–192°. Potassium carbonate (7.75 g) was added to a solution of 4-methyl-5-[(2-aminoethyl)thiomethyl]imidazole dihydrochloride (14.6 g) in water (120 ml). The solution was stored at room temperature for 15 minutes and methyl isothiocyanate (5.15 g) was added. After heating under reflux for 30 minutes, the solution was slowly cooled to 5°. The product was collected and recrystallised from water to give N-methyl-N'-[2-((5-methyl-4-imidazolyl)methylthio)ethyl]thiourea, m.p.150°–152°.

EXAMPLE 7 a. A solution of 4-methyl-5-[(2-aminoethyl)thiomethyl]imidazole (17.0 g) and N-cyano-N',S-dimethylisothiourea (11.2 g) in acetonitrile (500 ml) was heated under reflux for 24 hours. Following concentration, the residue was chromatographed on a column of silica gel with acetonitrile as eluant and the product obtained was finally recrystallised from acetonitrile-ether to yield N-cyano-N'-methyl-N''-[2-((5-methyl-4-imidazolyl)methylthio)ethyl]guanidine, m.p. 141°–142°.

b. A solution of 4-methyl-5-[(2-aminoethyl)thiomethyl]imidazole (23.4 g) in ethanol was added slowly to a solution of dimethyl-N-cyanoimidodithiocarbonate (20.0 g) in ethanol, with stirring at room temperature. The mixture was set aside overnight at room temperature. Filtration afforded N-cyano-N'-[2-((5-methyl-4-imidazolyl)methylthio)ethyl]-S-methylisothiourea, m.p. 148°–150°. The filtrate was concentrated under reduced pressure and the mixture was triturated with cold water and the solid obtained, filtered off and recrystallised twice from isopropyl alcohol/ether to yield further product, m.p. 148°–150°.

A solution of methylamine in ethanol (33%, 75 ml) was added to a solution of N-cyano-N'-[2-((5-methyl-4-imidazolyl)methylthio)ethyl]-S-methylisothiourea (10.1 g) in ethanol (30 ml). The reaction mixture was set aside at room temperature for 2.5 hours. Following concentration under reduced pressure, the residue was recrystallised twice from isopropyl alcohol/petroleum ether, affording N-cyano-N'-methyl-N''-[2-((5-methyl-4-imidazolyl)methylthio)ethyl]guanidine, m.p. 141°–143°.

What we claim is:

1. A process for the production of a 4-(hydroxymethyl)imidazole derivative of formula

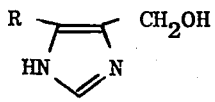

wherein R is hydrogen or lower alkyl, which comprises electrochemically reducing a 4-imidazolecarboxylic acid of the formula

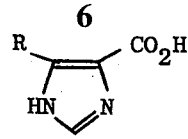

wherein R is hydrogen or lower alkyl in a protic solvent which is an aqueous solution of a strong acid using an inert cathode with a high hydrogen overvoltage.

2. A process according to claim 1 wherein R is methyl.

3. A process according to claim 1 wherein the cathode is lead or mercury.

4. A process according to claim 1 wherein the cathode is lead.

5. A process according to claim 1 wherein the solvent is an aqueous soltuion of sulphuric or hydrochloric acid.

6. A process according to claim 1 wherein the solvent is sulphuric acid, hydrochloric acid, hydrobromic acid, phosphoric acid, perchloric acid, trifluoroacetic acid or trichloroacetic acid.

* * * * *